(12) United States Patent
Hoshino et al.

(10) Patent No.: US 6,358,537 B1
(45) Date of Patent: *Mar. 19, 2002

(54) DEODORANT AND ANTIMICROBIAL DISPERSIONS

(75) Inventors: Akira Hoshino; Mikio Saji; Kozaburo Hayashi, all of Tokyo (JP)

(73) Assignee: Dainichiseika Color & Chemicals Mfg. Co, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/563,490

(22) Filed: May 3, 2000

(51) Int. Cl.[7] ............... A01N 59/06; A01N 25/00; A01N 33/08; A01N 59/00; A61L 9/01

(52) U.S. Cl. ............. 424/692; 424/76.1; 424/76.8; 424/688; 424/722; 424/724; 514/727; 514/738; 514/772.3; 514/782; 514/975

(58) Field of Search ............... 424/76.1, 76.8, 424/688, 692, 693, 722, 724; 514/699, 727, 738, 772.3, 782, 975

(56) References Cited

U.S. PATENT DOCUMENTS

| | | | |
|---|---|---|---|
| 3,885,961 A | 5/1975 | Kimura et al. | 430/96 |
| 3,996,142 A | 12/1976 | White et al. | 524/433 |
| 4,154,618 A | 5/1979 | Burke | 106/31.67 |
| 4,166,744 A | 9/1979 | Smith | 106/35 |
| 4,316,969 A | 2/1982 | Koyama et al. | 525/145 |
| 4,454,050 A | 6/1984 | Bertell | 508/219 |
| 4,735,972 A | 4/1988 | Shigematsu et al. | 523/102 |
| 4,757,099 A | 7/1988 | Hoshino et al. | 523/102 |
| 4,863,987 A | 9/1989 | Hoshino et al. | 524/293 |
| 4,880,852 A | 11/1989 | Hoshino et al. | 523/102 |
| 4,931,360 A | 6/1990 | Hoshino et al. | 428/328 |
| 5,063,256 A | 11/1991 | Hoshino et al. | 523/102 |
| 5,624,906 A | * 4/1997 | Vermeer | 514/23 |

* cited by examiner

*Primary Examiner*—Jose' G. Dees
*Assistant Examiner*—Frank Choi
(74) *Attorney, Agent, or Firm*—Oblon, Spivak, McClelland, Maier & Neustadt, P.C.

(57) ABSTRACT

A deodorant and antimicrobial dispersion is formed of a deodorant and antimicrobial component, a binder resin and an aqueous or oily liquid medium. The deodorant and antimicrobial component comprises an oxide or hydroxide of an alkaline earth metal, hydrated silica, and a cationic surfactant.

5 Claims, No Drawings

DEODORANT AND ANTIMICROBIAL DISPERSIONS

BACKGROUND OF THE INVENTION a) Field of the Invention

This invention relates to deodorant and antimicrobial dispersions, and more specifically, to deodorant and antimicrobial dispersions useful by themselves as liquid deodorant and antimicrobial agents and useful for imparting deodorizing power and antimicrobial activity to various base materials such as paints, synthetic fibers, synthetic resins and paper.

b) Description of the Related Art

Numerous deodorant and antimicrobial agents have been used to date in various fields. In particular, a variety of products such as films, wall paper, decorated plywood, building materials, fibers, nonwoven fabrics and clothing are required neither to give off offensive odor nor to permit growth of bacteria, fungi and the like, that is, to have so-called deodorizing power and antimicrobial activity in many instances.

In recent years, there is an ever-increasing demand for the amenity of living space. In view of the crowding of houses due to urbanization and also of the living environment of a closed house or building structure constructed of concrete and aluminum sash windows, it has become an indispensable condition for clean-environment life that visual, olfactory and hygienic unpleasant feeling be removed.

Described specifically, formaldehyde-linked health disturbances have posed problems in recent years. The odor of formaldehyde has already become a social problem as "sick house syndrome" in a living environment of a closed house structure, especially in a newly-built house. This problem is attributed to formaldehyde given off from newly-developed building materials. Various products—such as wall paper, decorated plywood, building materials, fibers, nonwoven fabrics and clothing—are hence required to have a function to remove formaldehyde. Further, from the viewpoint of, such products are also required to be equipped with an antimicrobial and antifungal function.

SUMMARY OF THE INVENTION

An object of the present invention is, therefore, to provide a deodorant and antimicrobial dispersion which can impart excellent deodorizing power and antimicrobial activity to various materials.

The above-described object can be achieved by the present invention to be described subsequently herein. Namely, the present invention provides a deodorant and antimicrobial dispersion comprising a deodorant and antimicrobial component, a binder resin and an aqueous or oily liquid medium, wherein the deodorant and antimicrobial component comprises an oxide or hydroxide of an alkaline earth metal, hydrated silica, and a cationic surfactant.

The deodorant and antimicrobial dispersion can be obtained by dispersing the specific deodorant and antimicrobial component in the aqueous or oily liquid medium in which the binder resin is contained. The dispersion can be sprayed without causing contamination. Especially, the deodorant and antimicrobial dispersion can be preferably used for the a production of base paper for decorated facing plates, woven fabrics, base paper for wall paper, and the like, all of which are provided with deodorizing power and antimicrobial activity.

The deodorant and antimicrobial dispersion is effective for the deodorization of acetoaldehyde odor, formaldehyde odor, acetic acid odor and the like out of various offensive odors and also for the inhibition of growth of bacteria, fungi and the like. Further, the deodorant and antimicrobial dispersion according to the present invention can impart excellent deodorizing power and antimicrobial activity to various materials.

DETAILED DESCRIPTION OF THE INVENTION AND PREFERRED EMBODIMENTS

The present invention will next be described more specifically based on preferred embodiments.

The deodorant and antimicrobial component, which makes up the deodorant and antimicrobial dispersion according to the present invention, comprises, in combination, an oxide or hydroxide of an alkaline earth metal, hydrated silica, and a cationic surfactant. Illustrative of the alkaline earth metal oxide or hydroxide are the oxides and hydroxides of barium, calcium, magnesium and the like, with magnesium hydroxide being particularly effective.

This alkaline earth metal oxide or hydroxide may be used preferably in such a proportion that, when the total amount of the deodorant and antimicrobial component is supposed to be 100 parts by weight, it amounts to 80 to 40 parts by weight. A proportion of the alkaline earth metal oxide or hydroxide smaller than the above range leads to insufficient performance in that conversion of aldehydes, especially formaldehyde into formose becomes slower. On the other hand, a proportion of the alkaline earth metal oxide or hydroxide greater than the above range also leads to insufficient performance in that the proportion of a substance adapted to undergo an addition reaction with formaldehyde for the removal of formaldehyde, that is, the cationic surfactant in the composition decreases, thereby lowering the deodorizing reaction velocity of aldehydes and resulting in insufficient fast-acting property.

The hydrated silica for use in the present invention is represented by the empirical formula $SiO_2 \cdot nH_2O$, and is in the form of secondary particles formed as a result of flocculation of fine silica particles having many silanol groups on surfaces thereof. Such hydrated silica is a flocculate of ultrafine particles of hydrated silica, which is available from a reaction of sodium silicate with a mineral acid, and contains a number of voids between particles. These voids effectively act for the adsorption of offensive odor components. Upon production of deodorant and antimicrobial, decorated facing plates, these voids also contribute to improvements in the impregnation of the hydrated silica with a base material for the decorated facing plates, such as a melamine resin, polyester resin or urethane resin, which is used in the production.

Such hydrated silica is available, for example, from Mizusawa Industrial Chemicals, Inc., Tokyo, Japan under the trade names of "P-801", "P-802", "P-526", "P-527", "P-$_{603}$", "P-604", "P-554A", "P-73", "P-78A", "P-78D", "P-78F", "P-707", "P-740", "P-752", "P-50", "P-766", "C-1", "S-0", "NP-8", "P-802Y", "P-832", "P-87", "P-363", "C-002", "C-402" and "C-484", all of which are usable in the present invention.

The above-described hydrated silica may be used preferably in such a proportion that, when the total amount of the deodorant and antimicrobial component is supposed to be 100 parts by weight, it amounts to 50 to 10 parts by weight. A proportion of the hydrated silica smaller than the above range leads to insufficient performance in that the deodorizing reaction velocity of aldehydes becomes slower, resulting in insufficient fast-acting property. On the other hand, a proportion of the hydrated silica greater than the above range also leads to insufficient performance in that, when used in paints or the like, the paints and the like are provided with poor flowability and especially, with insufficient shelf stability.

As the cationic surfactant for use in the present invention, one represented by the empirical formula HO—R—NHCH$_2$CH$_2$OH in which R is a C$_{12}$–C$_{14}$ alkylene group is preferred. The cationic surfactant reacts with an aldehyde group of formaldehyde or the like, thereby converting such an aldehyde compound into an odorless compound.

Such cationic surfactants are available from Miyoshi Oil & Fat Co., Ltd., Tokyo, Japan under the trade names of "Miyocol 368E", "Miyocol QX-33N", "Duspar 125B", "Duspar 125B", "Duspar 125B" and "Duspar 1400B", all of which are usable in the present invention.

The above-described cationic surfactants can be used either singly or in combination. They, however, include some compounds which, when formed into dispersions, may not be sufficient in dispersibility, stability, thermal stability, light fastness, processability and/or the like. Upon using the deodorant and antimicrobial dispersion of this invention for various applications, heat resistance is also important in connection with processability. From this viewpoint, "Duspar 125B" and "Duspar 125BN" are particularly preferred.

The above-described cationic surfactant may be used preferably in such a proportion that, when the total amount of the deodorant and antimicrobial component is supposed to be 100 parts by weight, it amounts to 0.1 to 30 parts by weight. If the cationic surfactant is used in a proportion smaller than the above range, the resulting composition is insufficient in performance in that the velocity of deodorizing reaction with aldehydes becomes slower and the fast-acting property is insufficient. If the cationic surfactant is used in a proportion greater than the above range, on the other hand, the resulting deodorant and antimicrobial dispersion is insufficient in performance in that, when it is used in a paint, coated films are provided with reduced physical properties and especially, insufficient resin impregnation, insufficient hardening and the like take place upon forming melamine facing plates.

The deodorant and antimicrobial dispersion according to the present invention can be obtained by dispersing the deodorant and antimicrobial component in the aqueous or oily liquid medium which contains the binder resin. Examples of the aqueous liquid medium can include water, and mixtures of water water-soluble organic solvents. Illustrative of such water-soluble organic solvents are methanol, ethanol, propanol, acetone, methyl ethyl ketone, ethylene glycol, diethylene alcohol, their acetates and lower alcohol ethers, dioxane, pyrrolidone, dimethylformamide, formamide, and dimethyl sulfoxide.

On the other hand, examples of the oily liquid medium can include organic solvents commonly employed in paints and printing inks. Specific examples can include ketones such as acetone, methyl ethyl ketoneandmethyl isobutyl ketone; esters such as ethyl acetate, butyl acetate, methyl lactate and butyl acetate; hydrocarbons such as toluene and xylene; and other organic solvents.

As illustrative binder resins for use in the present invention, acrylic resins, vinyl acetate resin, and binder resins used in a variety of conventional water-based paints and printing inks are all usable. The binder resin may be added at any concentration, but in general, may preferably be added in a proportion of from 10 to 1,000 parts by weight per 100 parts by weight of the deodorant and antimicrobial component. The binder resin may be dissolved in the aqueous or oily liquid medium, or may be dispersed or emulsified in the liquid medium.

The deodorant and antimicrobial dispersion according to the present invention can be obtained by dissolving or dispersing the deodorant and antimicrobial component in the liquid medium containing the conventionally-known binder resin such that the concentration of the deodorant and antimicrobial component falls preferably within a range of from about 5 to 50 wt. %, more preferably within a range of from 10 to 30 wt. % in terms of solids. A colorant such as a dye or pigment can also be added to the deodorant and antimicrobial dispersion according to the present invention.

To disperse or dissolve the deodorant and antimicrobial component in the aqueous or oily liquid medium containing the binder resin, dispersers conventionally used in the technical field of pigment dispersion, such as ball mills, speed line mills, sandmills, roll mills and paint shakers, are all usable.

The present invention will next be described more specifically based on describing examples and a comparative example, in which all designations of "part or parts" and "%" are on weight basis.

EXAMPLE 1

Thirty (30) parts of a 6:3:1, by weight, mixture of magnesium hydroxide, hydrated silica ("P-766", trade name) and a cationic surfactant ("Duspar 125B", trade name) were added to 70 parts of water. The resultant mixture was subjected to dispersion treatment for 1 hour by a paint shaker, whereby a deodorant and antimicrobial aqueous dispersion was obtained. Fifty (50) parts of the dispersion were added and mixed with 50 parts of a paint vehicle composed of a colorless acrylic resin emulsion, whereby a deodorant and antimicrobial coating formulation was obtained.

The deodorant and antimicrobial coating formulation was coated at 3 g/m$^2$ in terms of the deodorant and antimicrobial component on a nonwoven fabric by a roll coater and was then dried, whereby a deodorant and antimicrobial sheet was obtained. Deodorant power and antimicrobial activity of the sheet were tested as will be described subsequently herein.

EXAMPLE 2

The deodorant and antimicrobial coating formulation obtained in Example 1 was coated at 3 g/m$^2$ in terms of the deodorant and antimicrobial component on a base paper for a melamine facing plate, said base paper having had been obtained by impregnating a thin decorating paper sheet (40 g/m$^2$) with a melamine resin, by a gravure printing press and was then dried, whereby a deodorant and antimicrobial sheet was obtained. Deodorant power and antimicrobial activity of the sheet were tested as will be described subsequently herein.

EXAMPLE 3

Thirty (30) parts of a 7:2:1, by weight, mixture of magnesium hydroxide, hydrated silica ("P-740", trade name) and a cationic surfactant ("Duspar 125B", trade name) were added to 70 parts of water. The resultant mixture was subjected to dispersion treatment for 1 hour by a paint shaker, whereby a deodorant and antimicrobial aqueous dispersion was obtained. Fifty (50) parts of the dispersion were added and mixed with 50 parts of a paint vehicle composed of a colorless acrylic resin emulsion, whereby a deodorant and antimicrobial coating formulation was obtained.

The deodorant and antimicrobial coating formulation was coated at 3 g/m$^2$ in terms of the deodorant and antimicrobial component on a nonwoven fabric by a gravure printing press and was then dried, whereby a deodorant and antimicrobial sheet was obtained. Deodorant power and antimicrobial activity of the sheet were tested as will be described subsequently herein.

EXAMPLE 4

The deodorant and antimicrobial coating formulation obtained in Example 3 was coated at 3 g/m$^2$ in terms of the deodorant and antimicrobial component on a base paper for a melamine facing plate, said base paper having had been obtained by impregnating a thin decorating paper sheet (40 g/m$^2$) with a melamine resin, by a roll coater and was then dried. The melamine resin was hardened under heat, whereby a deodorant and antimicrobial sheet was obtained. Deodorant power and antimicrobial activity of the sheet were tested as will be described subsequently herein. Incidentally, the hardening of the melamine resin under heat was conducted by pressing the coated base paper at 140° C. for 20 minutes under 4 kg/cm$^2$.

EXAMPLE 5

Thirty (30) parts of a 4:4:2, by weight, mixture of magnesium hydroxide, hydrated silica ("P-752", trade name) and a cationic surfactant ("Duspar 125B", trade name) were added to 70 parts of water. The resultant mixture was subjected to dispersion treatment for 1 hour by a paint shaker, whereby a deodorant and antimicrobial aqueous dispersion was obtained. Fifty (50) parts of the dispersion were added and mixed with 50 parts of a paint vehicle composed of a colorless acrylic resin emulsion, whereby a deodorant and antimicrobial coating formulation was obtained.

The deodorant and antimicrobial coating formulation was coated at 3 g/m$^2$ in terms of the deodorant and antimicrobial component on a nonwoven fabric by a roll coater and was then dried, whereby a deodorant and antimicrobial sheet was obtained. Deodorant power and antimicrobial activity of the sheet were tested as will be described subsequently herein.

EXAMPLE 6

Thirty (30) parts of a 5:2:3, by weight, mixture of magnesium hydroxide, hydrated silica ("P-707", trade name) and a cationic surfactant ("Duspar 125B", trade name) were added to 70 parts of a topcoating (urethane resin; "PTC", trade name; product of Dainichiseika Color & Chemicals Mfg. Co., Ltd., Tokyo, Japan). The resultant mixture was subjected to dispersion treatment for 1 hour by a paint shaker, whereby an oil-based, deodorant and antimicrobial coating formulation was obtained.

After a thin decorating paper sheet (40 g/m$^2$) was printed solid and also in a pattern with a general nitrocellulose-alkyd ink, the deodorant and antimicrobial coating formulation was coated at 3 g/M$^2$ in terms of the deodorant and antimicrobial component on a surface of the printed thin decorating paper sheet by a gravure printing press and was then dried, whereby a deodorant and antimicrobial sheet was obtained. Next, the above-obtained deodorant and antimicrobial sheet was laminated on an MDF (main distribution frame) plywood by using a urea-melamine bond, whereby a deodorant and antimicrobial decorated plywood was obtained. Deodorant power and antimicrobial activity of the decorated plywood were tested as will be described subsequently herein.

EXAMPLE 7

Thirty (30) parts of a 6:3:1, by weight, mixture of magnesium hydroxide, hydrated silica ("P-832", trade name) and a cationic surfactant ("Duspar 125B", trade name) were added to 70 parts of water. The resultant mixture was subjected to dispersion treatment for 1 hour by a paint shaker, whereby a deodorant and antimicrobial aqueous dispersion according to the present invention was obtained. Fifty (50) parts of the dispersion were added and mixed with 50 parts of a paint vehicle composed of a colorless acrylic resin emulsion, whereby a deodorant and antimicrobial coating formulation was obtained.

The deodorant and antimicrobial coating formulation was coated at 3 g/m$^2$ in terms of the deodorant and antimicrobial component on a wall paper made of polyvinyl chloride resin by a roll coater and was then dried, whereby a deodorant and antimicrobial wall paper made of polyvinyl chloride resin was obtained. Deodorant power and antimicrobial activity of the wall paper made of polyvinyl chloride resin were tested as will be described subsequently herein.

Deodorizing and antimicrobial effects of the various products obtained in Examples 1–7 were investigated by the following testing methods, respectively. The results are summarized in Table 1 to Table 5.

[Deodorizing Performance Testing Methods]

(Acetic acid deodorization test)

In a 300-mL Erlenmeyer flask, a 2% aqueous solution of acetic acid (2.5 μL) was placed, followed by the addition of a sample. The flask was left over at 25° C., and subsequent to an elapse of a predetermined time, the concentration of acetic acid still remaining in the flask was measured using a Kitagawa gas detector. The results are presented in Table 1.

(Formaldehyde deodorization test)

In a 300-mL Erlenmeyer flask, a 3.5% aqueous solution of formaldehyde (1 μL) was placed, followed by the addition of a sample. The flask was left over at 25° C., and subsequent to an elapse of a predetermined time, the concentration of formaldehyde still remaining in the flask was measured using the Kitagawa gas detector. The results are presented in Table 2.

(Acetoaldehyde deodorization test)

In a 300-mL Erlenmeyer flask, a 2.5% aqueous solution of acetoaldehyde (1 μL) was placed, followed by the addition of a sample. The flask was left over at 25° C., and subsequent to an elapse of a predetermined time, the concentration of acetoaldehyde still remaining in the flask was measured using the Kitagawa gas detector. The results are presented in Table 3.

TABLE 1

Results of Acetic Acid Deodorization Test

| | Concentration of acetic acid (ppm) | | | |
| --- | --- | --- | --- | --- |
| | 5 min later | 30 min later | 120 min later | Test sample |
| Blank | 45 | 45 | 45 | Sheet piece (50 mm × 200 mm) |
| Example 1 | 2 | Not detected | Not detected | Sheet piece (50 mm × 200 mm) |
| Example 2 | 1 | Not detected | Not detected | Sheet piece (50 mm × 200 mm) |
| Example 3 | 2 | Trace | Not detected | Sheet piece (50 mm × 200 mm) |

TABLE 1-continued

Results of Acetic Acid Deodorization Test

Concentration of acetic acid (ppm)

| | 5 min later | 30 min later | 120 min later | Test sample |
|---|---|---|---|---|
| Example 4 | 3 | Not detected | Not detected | Sheet piece (50 mm × 200 mm) |
| Example 5 | Not detected | Not detected | Not detected | Sheet piece (50 mm × 200 mm) |
| Example 6 | Not detected | Not detected | Not detected | Sheet piece (50 mm × 200 mm) |
| Example 7 | Not detected | Not detected | Not detected | Sheet piece (50 mm × 200 mm) |
| Comp. Ex. | 10 | 5 | 5 | Sheet piece (50 mm × 200 mm) |

In the blank, a sheet prepared in a similar manner as in Example 1 except that the deodorant and antimicrobial composition was not used was used as a test sample.
In the comparative example, a sheet prepared in a similar manner as in Example 1 except that the deodorant and antimicrobial component was not added with the cationic surfactant was used as a test sample.
These footnotes will apply equally to Table 2 and Table 3.

TABLE 2

Results of Formaldehyde Deodorization Test

Concentration of formaldehyde (ppm)

| | 5 min later | 30 min later | 120 min later | Test sample |
|---|---|---|---|---|
| Blank | 105 | 105 | 105 | Sheet piece (50 mm × 200 mm) |
| Example 1 | 20 | 15 | 10 | Sheet piece (50 mm × 200 mm) |
| Example 2 | 25 | 10 | 8 | Sheet piece (50 mm × 200 mm) |
| Example 3 | 20 | 8 | 3 | Sheet piece (50 mm × 200 mm) |
| Example 4 | 15 | 5 | 1 | Sheet piece (50 mm × 200 mm) |
| Example 5 | Not detected | Not detected | Not detected | Sheet piece (50 mm × 200 mm) |
| Example 6 | Not detected | Not detected | Not detected | Sheet piece (50 mm × 200 mm) |
| Example 7 | Not detected | Not detected | Not detected | Sheet piece (50 mm × 200 mm) |
| Comp. Ex. | 60 | 50 | 50 | Sheet piece (50 mm × 200 mm) |

TABLE 3

Results of Acetoaldehyde Deodorization Test

Concentration of acetoaldehyde (ppm)

| | 5 min later | 30 min later | 120 min later | Test sample |
|---|---|---|---|---|
| Blank | 35 | 35 | 35 | Sheet piece (50 mm × 200 mm) |
| Example 1 | 10 | 5 | 1 | Sheet piece (50 mm × 200 mm) |
| Example 2 | 15 | 8 | 3 | Sheet piece (50 mm × 200 mm) |
| Example 3 | 9 | 5 | 2 | Sheet piece (50 mm × 200 mm) |
| Example 4 | 5 | 3 | Trace | Sheet piece (50 mm × 200 mm) |
| Example 5 | 3 | Trace | Not detected | Sheet piece (50 mm × 200 mm) |
| Example 6 | 1 | Not detected | Not detected | Sheet piece (50 mm × 200 mm) |
| Example 7 | 1 | Not detected | Not detected | Sheet piece (50 mm × 200 mm) |
| Comp. Ex. | 15 | 10 | 10 | Sheet piece (50 Mm × 200 mm) |

[Antimicrobial Test]
Tested Bacteria Strains
Gram-negative bacteria: *Escherichia coli* IFO 3972
Gram-positive bacteria: *Staphylococcus aureus* IFO 12732
Testing Method
Preculture: Cultured at 37° C. under shaking on nutrient broth liquid medium (*E. coli*: 16 hours, *S. aureus*: 12 hours).
Antimicrobial test: A sterilized sample (about 50×50 mm) was dried and then placed in a sterilized Petri dish. On the side, the above-described precultures were diluted to prepare the inocula shown in Table 4 an Table 5, respectively. In the case of the preculture of *E. coli*, the inoculum was prepared by diluting the preculture with a solution such that the viable cell count per mL was adjusted to 3.1×105. The solution had been prepared by diluting the nutrient broth liquid medium with phosphate buffer (pH 7.2) such that the concentrations of its nutrients were lowered to 1/500. In the case of the preculture of *S. aureus*, on the other hand, the inoculum was prepared by diluting the preculture with a solution such that the viable cell count per mL was adjusted to $8.5 \times 10^4$. The solution had been prepared by diluting the nutrient broth liquid medium with phosphate buffer (pH 7.2) such that the concentrations of its nutrients were lowered to 1/50. Concerning each cell strain, the inoculum the viable cell count of which had been adjusted as described above was inoculated to a surface of each sample at four diagonal corners of the sample and also at a center of the sample in an amount of 0.1 mL per location, that is, in a total amount of 0.5 mL. After incubation at 30±1° C. and a relative humidity of 90% or higher for 24 hours, cells were washed out with phosphate buffer (4.5 mL). By the pour plate method, the viable cell count of the test solution was determined using nutrient agar. Further, as a control, a Petri dish with the inoculum alone dropped therein was also tested.

TABLE 4

Results of Antimicrobial Test on *E. coli*

| Sample | Viable cell count (cells/mL) | Inhibition rate (%) |
| --- | --- | --- |
| Inoculum (initial viable cell count) | $2.9 \times 10^5$ | — |
| Control | $1.8 \times 10^5$ | — |
| Example 1 | <10 | >99.99 |
| Example 2 | <10 | >99.99 |
| Example 3 | <10 | >99.99 |
| Example 4 | <10 | >99.99 |
| Example 5 | <10 | >99.99 |
| Example 6 | <10 | >99.99 |
| Example 7 | <10 | >99.99 |
| Comparative Example | $7.7 \times 10^6$ | 0 |

In the control, the inoculum was left over without addition of any sample to the Petri.
In the comparative example, a sheet prepared in a similar manner as in Example 1 except that the deodorant and antimicrobial component was not added with the cationic surfactant was used as a test sample.
These footnotes will apply equally to Table 5.

TABLE 5

Results of Antimicrobial Test on *S. aureus*

| Sample | Viable cell count (cells/mL) | Inhibition rate (%) |
| --- | --- | --- |
| Inoculum (initial viable cell count) | $8.3 \times 10^4$ | — |
| Control | $6.5 \times 10^4$ | — |
| Example 1 | <10 | >99.99 |
| Example 2 | <10 | >99.99 |
| Example 3 | <10 | >99.99 |
| Example 4 | <10 | >99.99 |
| Example 5 | <10 | >99.99 |
| Example 6 | <10 | >99.99 |
| Example 7 | <10 | >99.99 |
| Comparative Example | $6.6 \times 10^4$ | 0 |

EXAMPLE 8

Forty (40) parts of a paint vehicle composed of a colorless acrylic resin emulsion were added and mixed with 60 parts of a mixture consisting of magnesium hydroxide, hydrated silicate ("P-766", trade name) and a cationic surfactant ("Duspar 125B", trade name) at a weight ratio of 6:3:1. The resulting mixture was then formed into bead-shaped deodorant and antimicrobial granules of 4 mm in diameter by "Marumerizer" (trade mark, manufactured by Fuji Paudal Co., Ltd., Osaka, Japan).

Those bead-shaped deodorant and antimicrobial granules (100 g) were filled in a filter pocket of a vacuum cleaner ("CV-C45", trade name; manufactured by Hitachi, Ltd.), and in a room (temperature: 26° C., humidity: 75%), walls and a floor were swept clean by the vacuum cleaner. The concentration of formaldehyde in the room dropped from 0.279 ppm to 0.003 ppm (percent removal of formaldehyde: 80%), and in a closet, the concentration of formaldehyde dropped from 0.467 ppm to 0.003 ppm (percent removal of formaldehyde: 90%).

What is claimed is:

1. A deodorant and antimicrobial dispersion comprising a deodorant and antimicrobial component, a binder resin and an aqueous or oily liquid medium, wherein said deodorant and antimicrobial component comprises an oxide or hydroxide of an alkaline earth metal, hydrated silica, and a cationic surfactant, wherein said cationic surfactant is represented by the following empirical formula: HO—R—NHCH$_2$CH$_2$OH in which R is a $C_{12}$–$C_{14}$ alkylene group.

2. The deodorant and antimicrobial dispersion according to claim 1, wherein said deodorant and antimicrobial component comprises 80 to 40 parts by weight of said oxide or hydroxide of said alkaline earth metal, 50 to 10 parts by weight of said hydrated silica, and 0.1 to 30 parts by weight of said cationic surfactant, all parts based on 100 parts by weight of the deodorant and antimicrobial component.

3. The deodorant and antimicrobial dispersion according to claim 1, wherein said oxide or hydroxide of said alkaline earth metal is magnesium hydroxide.

4. The deodorant and antimicrobial dispersion according to claim 1, wherein an amount of said binder resin is from 10 to 1,000 parts by weight per 100 parts by weight of said deodorant and antimicrobial component.

5. The deodorant and antimicrobial dispersion according to claim 1, wherein a concentration of said deodorant and antimicrobial component in said dispersion is from 5 to 50 wt %.

* * * * *